(12) United States Patent
Yabusaki (10) Patent No.: US 11,717,152 B2
(45) Date of Patent: Aug. 8, 2023

(54) TEAR FLUID LAYER EVALUATION METHOD, COMPUTER PROGRAM, AND DEVICE

(71) Applicant: KOWA COMPANY, LTD., Aichi (JP)

(72) Inventor: Katsumi Yabusaki, Higashimurayama (JP)

(73) Assignee: KOWA COMPANY, LTD., Aichi (JP)

( * ) Notice: Subject to any disclaimer, the term of this patent is extended or adjusted under 35 U.S.C. 154(b) by 720 days.

(21) Appl. No.: 16/627,683

(22) PCT Filed: Jul. 3, 2018

(86) PCT No.: PCT/JP2018/025170
§ 371 (c)(1),
(2) Date: Dec. 30, 2019

(87) PCT Pub. No.: WO2019/009277
PCT Pub. Date: Jan. 10, 2019

(65) Prior Publication Data
US 2020/0154995 A1    May 21, 2020

(30) Foreign Application Priority Data
Jul. 4, 2017    (JP) .................................. 2017-131142

(51) Int. Cl.
*A61B 3/10*    (2006.01)
*A61B 3/12*    (2006.01)
(Continued)

(52) U.S. Cl.
CPC ................ *A61B 3/101* (2013.01); *A61B 3/14* (2013.01); *G06T 7/0012* (2013.01); *G06T 2207/10024* (2013.01); *G06T 2207/30041* (2013.01)

(58) Field of Classification Search
CPC ......... A61B 3/02; A61B 3/102; A61B 3/1025; A61B 3/113; A61B 3/1015; A61B 3/1225; A61B 3/024
(Continued)

(56) References Cited

U.S. PATENT DOCUMENTS 6,299,305 B1    10/2001    Miwa
9,959,635 B2    5/2018    Nakai
(Continued)

FOREIGN PATENT DOCUMENTS

CN    106510615 A    3/2017
CN    106557735 A    4/2017
(Continued)

OTHER PUBLICATIONS

Extended European Search Report dated Mar. 2, 2021, issued in European Patent Application No. 18827363.5.
(Continued)

*Primary Examiner* — Dawayne Pinkney
(74) *Attorney, Agent, or Firm* — McDermott Will & Emery LLP (57) ABSTRACT

A method, a computer program and a device for evaluating a tear fluid layer non-invasively. The method, computer program, and device include a step of detecting a time when color information in a predetermined region in a tear fluid layer interference fringe image changes by a threshold value or more as an eyelid opening time, a step of extracting an image at the time when the predetermined time has passed from the eyelid opening time as an extracted image from the tear fluid interference fringe images, a determination value calculation step of calculating a determination value from the color information in a pixel in a local region by scanning a predetermined target region, a step of detecting a corresponding pixel by comparing the calculated determination
(Continued)

value and a threshold value, and an evaluation step of evaluating tear fluid layer breakdown by comparing the detected pixel and a threshold value.

10 Claims, 4 Drawing Sheets

(51) Int. Cl.
*A61B 3/02* (2006.01)
*A61B 3/14* (2006.01)
*G06T 7/00* (2017.01)

(58) Field of Classification Search
USPC ....... 351/206, 200, 205, 209, 210, 221–223, 351/246
See application file for complete search history.

(56) References Cited

U.S. PATENT DOCUMENTS

| | | | |
|---|---|---|---|
| 2005/0162611 A1* | 7/2005 | Miwa | A61B 3/145 351/205 |
| 2008/0309872 A1 | 12/2008 | Hara et al. | |
| 2012/0300174 A1 | 11/2012 | Yokoi et al. | |
| 2015/0141278 A1* | 5/2015 | Hollman-Hewgley | G01N 1/30 435/7.1 |
| 2016/0338585 A1 | 11/2016 | Arieli et al. | |
| 2017/0091955 A1 | 3/2017 | Nakai | |
| 2017/0236259 A1* | 8/2017 | Park | G06T 5/006 382/167 |
| 2020/0074627 A1* | 3/2020 | Yokoi | A61B 3/101 |

FOREIGN PATENT DOCUMENTS

| | | |
|---|---|---|
| JP | H09-201334 A | 8/1997 |
| JP | 2000-237135 A | 9/2000 |
| JP | 2000-254099 A | 9/2000 |
| JP | 2001-309889 A | 11/2001 |
| JP | 2005-211173 A | 8/2005 |
| JP | 3699853 B2 | 9/2005 |
| JP | 2007-209370 A | 8/2007 |
| JP | 2011-156030 A | 8/2011 |
| JP | 2016-115119 A | 6/2016 |
| KR | 10-1542938 B1 | 8/2015 |
| WO | WO-2019031424 A1 * | 2/2019 ........... A61B 3/0008 |

OTHER PUBLICATIONS

"Definition of dry eye in Japan and revision of diagnostic criteria," Journal of the Eye, Dry Eye Society, 2016 Edition, vol. 34, No. 3, Mar. 31, 2017, pp. 309-313; with partial English translation.
First Office Action issued in corresponding Chinese Patent Application No. 201880044225.3, dated Jul. 2, 2021.
Shunji Nakao, "Dry Eye Diagnosis PPP (Preferred Pattern of Practice)", Dry Eye Society, Medical View Co., Ltd., May 1, 2002, pp. 41 to 45; with English translation.
"Definition of dry eye in Japan and revision of diagnostic criteria," Journal of the Eye, Dry Eye Society, 2016 edition, vol. 34, No. 3, Mar. 31, 2017, pp. 309-313.
International Search Report and Written Opinion issued in International Patent Application No. PCT/JP2018/025170 dated Sep. 18, 2018; with partial English translation.
Notice of Reasons for Refusal dated Dec. 13, 2022 issued in the corresponding Japanese Patent Application No. 2019-527716, with English translation.

* cited by examiner

TEAR FLUID LAYER EVALUATION METHOD, COMPUTER PROGRAM, AND DEVICE

CROSS-REFERENCE OF RELATED APPLICATIONS

This application is the U.S. National Phase under 35 U.S.C. § 371 of International Patent Application No. PCT/JP2018/025170, filed on Jul. 3, 2018, which in turn claims the benefit of Japanese Application No. 2017-131142, filed on Jul. 4, 2017, the entire disclosures of which Applications are incorporated by reference herein.

TECHNICAL FIELD

The present invention relates to a method, a computer program, and a device for evaluating a state and breakdown of a tear fluid layer in order to non-invasively determine dry eye.

BACKGROUND

An eyeball and an eyelid are protected by a tear fluid from entry of a foreign matter, drying, a damage due to friction, and the like. The tear fluid layer is composed of two layers, a liquid layer including water that occupies most of the tear fluid layer and a glycoprotein (mucin), and an oil layer covering the liquid layer. The oil layer prevents evaporation of the liquid layer by preventing the liquid layer from being in direct contact with the air. A component of the oil layer is secreted from the meibomian gland present in the eyelid. If the meibomian gland is damaged due to aging, inflammation, scratching, and the like, the oil layer is not properly formed, causing a symptom, so-called dry eye, due to failure to maintain the liquid layer.

As a method for determining dry eye, "Schirmer's test" and "BUT (Breakup time) test" are conventionally known. This "Schirmer's test" is a method in which a filter paper with a scale is placed between the conjunctiva and the lower eyelid, and, after maintaining this state for 5 minutes, an amount of the tear fluid absorbed in the filter paper after 5 minutes is quantitatively determined.

On the other hand, as described in Non-patent Literature 1, in the "BUT test," a fluorescent dye melted in a liquid layer of the tear fluid layer such as fluorescein is applied to an eye, and, after the fluorescence is excited by excitation light, a time from opening the eyelid to the breakdown of the liquid layer of the tear fluid is measured by a stopwatch or the like.

Such a diagnostic method of dry eye, in particular, the "Schirmer's test" is an invasive test in which a filter paper is placed between the conjunctiva and the lower eyelid, thus causing a problem of leaving an uncomfortable feeling or a foreign body sensation to the eye after the test. Further, in the "Schirmer's test," for example, placing the filter paper itself facilitates the secretion of the tear fluid by stimulating the eye, making it difficult to quantitatively determine the amount of the tear fluid at a normal time. Thus, there is a problem in which proper evaluation may not be achieved.

Further, on the other hand, in the "BUT test," the fluorescence may occur differently because of a difference in a location where the fluorescent dye in use is applied in the eye, an amount of the fluorescent dye, and the like. Further, in the first place, at which state or stage of the tear fluid layer the tear fluid breakdown is determined partially depends on subjectivity such as knowledge and experience of an actual examiner, and thus there is a problem of difficulty in avoiding a bias in measurement. Measurement of "BUT" highly involves a skill level or subjectivity of the examiner, making it difficult to obtain an objective measurement result.

An example of a conventional device for measuring "BUT" will be described here. A device in Patent Literature 1 non-invasively measures "BUT," thus so-called measuring "NIBUT," by projecting light emitted from a light source through a pattern projection plate onto the cornea of a subject, forming a corneal reflection image of the pattern on a television camera using an objective lens, and thereby detecting a state change of the corneal reflection image. The state change of the corneal reflection image is detected by detecting disturbance of signal waveforms of television scanning lines at a plurality of sites shown by the television scanning lines on the corneal reflection image displayed on a television monitor.

Further, a device described in Patent Literature 2 detects and measures a reflected light quantity of fluorescence from the cornea. The reflected light quantity is normally highest immediately after the opening of the eyelid and decreased over time as the tear fluid layer breakdown starts to occur. The device is thus configured to detect a region (area) of the tear fluid layer breakdown by setting a threshold value for the reflected light quantity.

CITATION LIST

Patent Literature

Patent Literature 1: Japanese Patent Application Laid-Open No. 2000-254099
Patent Literature 2: Japanese Patent No. 3699853

Non-Patent Literature

Non-Patent Literature 1: "Dry Eye Diagnosis PPP (pp. 41 to 45)" (first edition, first printing: May 1, 2002, Edited by: Dry Eye Society, Publisher: Shunji Nakao, Publishing Office: Medical View Co., Ltd.)

SUMMARY OF INVENTION

Technical Problem

However, the device in Patent Literature 1 requires, for example, a light source for irradiation to the cornea and a pattern projection plate and a configuration including a television camera and a television monitor, which makes the device complicated and imposes extra costs. Further, as for the device in Patent Literature 2, in a case where fluorescein is applied to an eye, there is a risk of involving a process which relies on experience or the like of the examiner as described above.

Further, in both devices in Patent Literature 1 and Patent Literature 2, evaluation may not be properly performed without obtaining a reflected light image or a reflected light quantity having clarity and brightness at a predetermined level or higher, and thus these devices require a fine adjustment of alignment, as well as an adjustment of a threshold value depending on a state of an individual subject and a surrounding environment.

Further, in recent years, in consideration of the above-described problems in the "Schirmer's test," instead of performing the "Schirmer's test" for diagnosing dry eye, a diagnosis standard in which dry eye is diagnosed simply by having "BUT" of 5 seconds or less is adopted in Asia regions including Japan.

If dry eye is determined by having "BUT" of 5 seconds or less in this manner, it means in another sense that dry eye can be determined by confirming a state of the tear fluid breakdown at a time when 5 seconds has passed from an eyelid opening time. Under such a circumstance, there is a need for a device and a method in accordance with the change described above in the diagnosis standard.

The present invention has been made in view of the conventional problems described above and an object of the present invention is to provide a device and a method capable of easily and surely diagnosing dry eye in a non-invasive manner by confirming a state of a tear fluid layer at a time when a predetermined time has passed from an eyelid opening time instead of precisely measuring "BUT."

Solution to Problem

A tear fluid layer evaluation method, computer program, and device according to the present invention include the following steps and means.
(1) The method, computer program, and device include a step of detecting a time when color information in a predetermined region in a tear fluid layer interference fringe image changes by a threshold value or more as an eyelid opening time, a step of extracting an image at the time when the predetermined time has passed from the eyelid opening time as an extracted image from the tear fluid interference fringe images, a determination value calculation step of calculating a determination value from the color information in a pixel in a local region by scanning a predetermined target region in the extracted image, a step of detecting a corresponding pixel by comparing the calculated determination value and a threshold value, and an evaluation step of evaluating tear fluid layer breakdown by comparing the detected pixel and a threshold value.
(2) In the (1) described above, the determination value is characterized by being a value indicating color variation calculated from the color information in the local region.
(3) In the (2) described above, the value indicating the color variation is characterized by being a value calculated as a variance or a deviation in the local region.
(4) In the (2) or (3) described above, the determination value is characterized by being a value obtained by dividing the value indicating the color variation in the local region by an average value of the color information in the local region.
(5) In the (1) described above, the determination value is characterized by being an average value of the color information in the local region.
(6) In the (1) to (5) described above, the predetermined time is characterized by being, for example, 5 seconds.
(7) In the (1) to (6) described above, the method, computer program, and device are characterized by including a predetermined time change step of allowing an examiner to change the predetermined time from the eyelid opening time.
(8) In the (1) to (7) described above, the extracted image is characterized by being extracted by acquiring the image at the time when the predetermine time has passed and its preceding or succeeding images having a plurality of frames with a predetermined number.

Advantageous Effects of Invention

The present invention exhibits the following advantageous effects. That is, an analysis is performed only on the image corresponding to the time when the predetermined time has passed from the eyelid opening time in the tear fluid layer interference fringe images, and thus a load applied to the device is lower than when measuring BUT, and, further, the analysis is adapted to the new standard for the diagnosis of dry eye.

Further, according to the present invention, it becomes possible to perform an objective evaluation in a non-invasive manner without a need for, for example, applying a fluorescent dye to an eye.

DESCRIPTION OF EMBODIMENTS

First Embodiment

<Acquisition of Tear Fluid Layer Interference Fringe Image>

Figure 4:
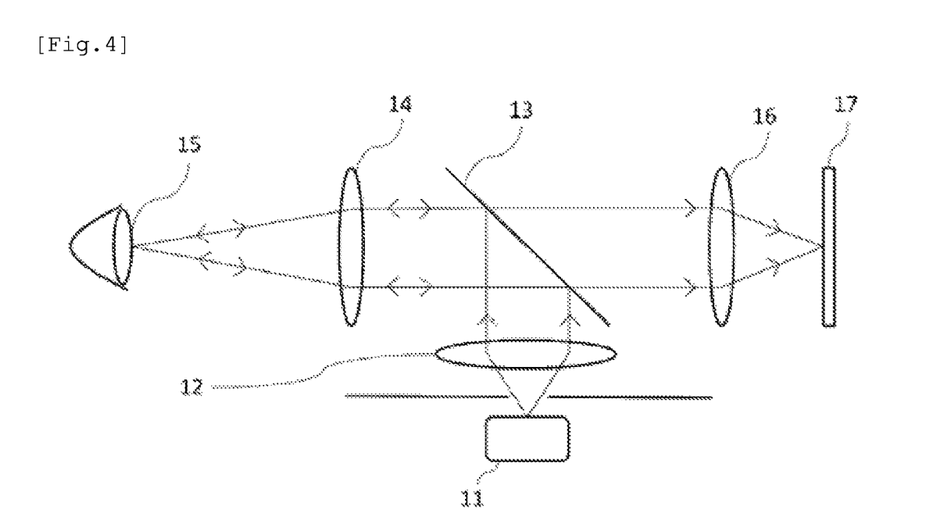
FIG. 4 is a schematic diagram illustrating a configuration of a tear fluid layer interference fringe image acquisition device.

As a device for acquiring the tear fluid layer interference fringe image on the surface of a cornea (a tear fluid layer interference fringe image acquisition device), a conventionally known device may be appropriately used as long as it can record the photographed image as digital data. For example, in the tear fluid layer interference fringe image acquisition device schematically shown in FIG. 4, a light beam, which has been emitted from a light source 11 and transmitted through a diaphragm, sequentially passes through a lens 12, a splitter 13, and an objective lens 14 and is condensed on an anterior eye portion 15 of a subject eye of a subject. Reflected light from the anterior eye portion 15 passes through the objective lens 14 and the splitter 13, so that an image is formed on an imaging element 17 via an imaging lens 16. Photographed data of the image formed on the imaging element 17 are subjected to a predetermined processing by an image processing engine and converted to image data and moving image data.

The tear fluid layer interference fringe image acquisition device is physically or logically connected to a tear fluid layer evaluation device according to the present invention. The tear fluid layer evaluation device includes a processing unit configured to compute and process data and a storing unit configured to store the image data, moving image data, and other data acquired by the tear fluid layer interference fringe image acquisition device. The storing unit stores a computer program and prescribed data for implementing the present invention, while the processing unit processes data according to a predetermined instruction by the computer program and the like.

A processing of the tear fluid layer interference fringe image thus obtained for determining dry eye will be described below. Note that, in the following description, unless otherwise specified, the tear fluid layer interference fringe images are moving images composed of a plurality of continuous frames recorded over a predetermined time and stored in a tear fluid layer evaluation device itself or a storage device connected thereto.

<Color Information of Image>

First, the color information usable in the present invention will be described. As an example of the color information, a method of using three color elements of red, green, and blue (numerical values in an RGB color space), which is used in many electronic image apparatuses, is mentioned.

Specifically, the color information in each pixel is luminance or brightness of color elements of red, green, and blue included in the pixel, and the luminance of at least one or more of the color elements of red, green, and blue in the RGB color space may be directly used, or, for example, the luminance may be converted into a gray scale and used.

Further, the color information may be a numerical value obtained by performing an arithmetic operation as necessary. For example, the numerical value may be calculated by combining two or more of the luminance of each of the color elements or by averaging two or more of the color elements. Alternatively, the numerical value may be obtained by multiplying each element by a different predetermined weighting coefficient.

Alternatively, the coefficient of variation may be individually calculated from three color elements of red, green, and blue, and, for example, the maximum value, the minimum value, or the second largest numerical value among them may be used.

The following description will be given on the basis of a case where the luminance in the RGB color space is used, but, as a matter of course, the color information in the present invention is not limited to the numerical values in the RGB color space. As the color information used in the present invention, luminance or brightness defined in the HSV color space, the HSB color space, the HLS color space, the HSL color space, or the like may be used.

Figure 2:
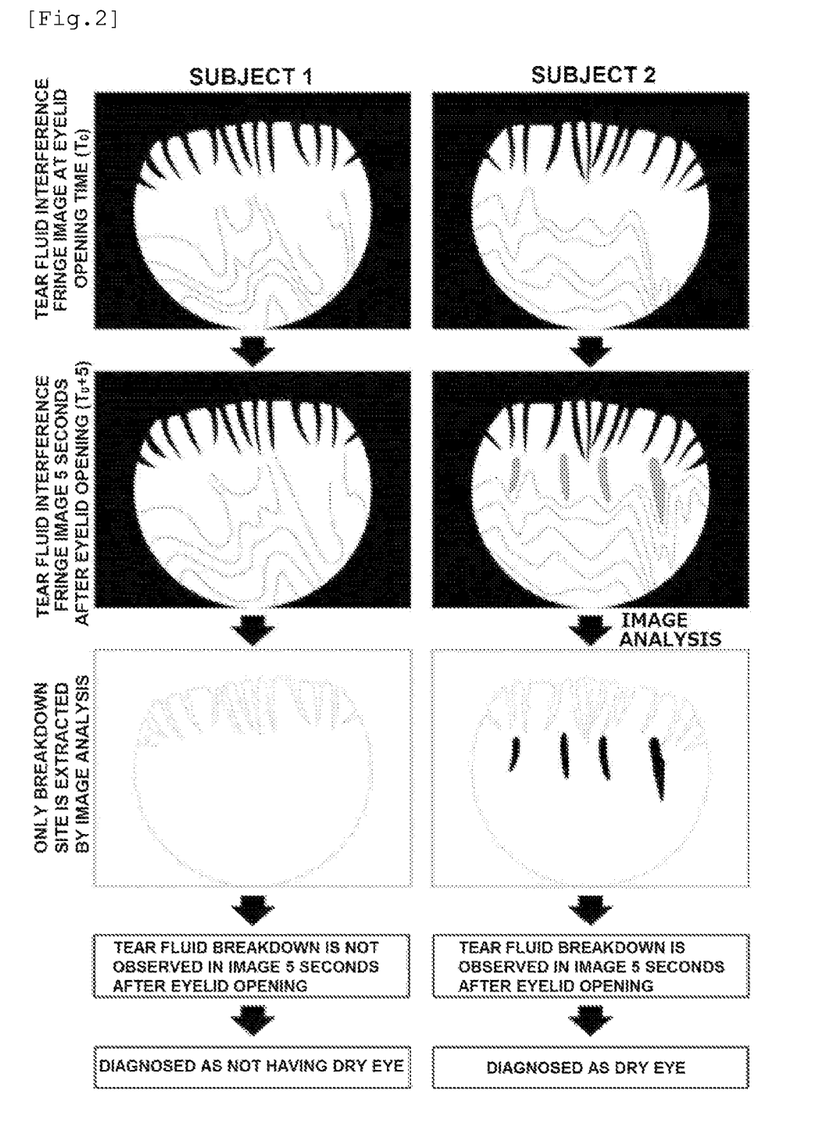
FIG. 2 is diagram schematically illustrating an example of tear fluid layer interference fringe images and image analysis thereof at an eyelid opening time and at a time when a predetermined time has passed in processings for determining dry eye.

Hereinafter, the content of each processing will be described in detail. FIG. 2 schematically shows an example of a flow of processings including a step of detecting the eyelid opening time on the basis of the predetermined color information in the tear fluid interference fringe images which have been photographed and stored, a step of extracting the image at the time when a predetermined time has passed from the eyelid opening time from the tear fluid interference fringe images as the extracted image, a step of calculating the determination value for determining the tear fluid layer breakdown from the predetermined color information in the extracted image, and a step of determining the tear fluid layer breakdown on the basis of the determination value.

<Detection of Eyelid Opening Time>

Figure 1:
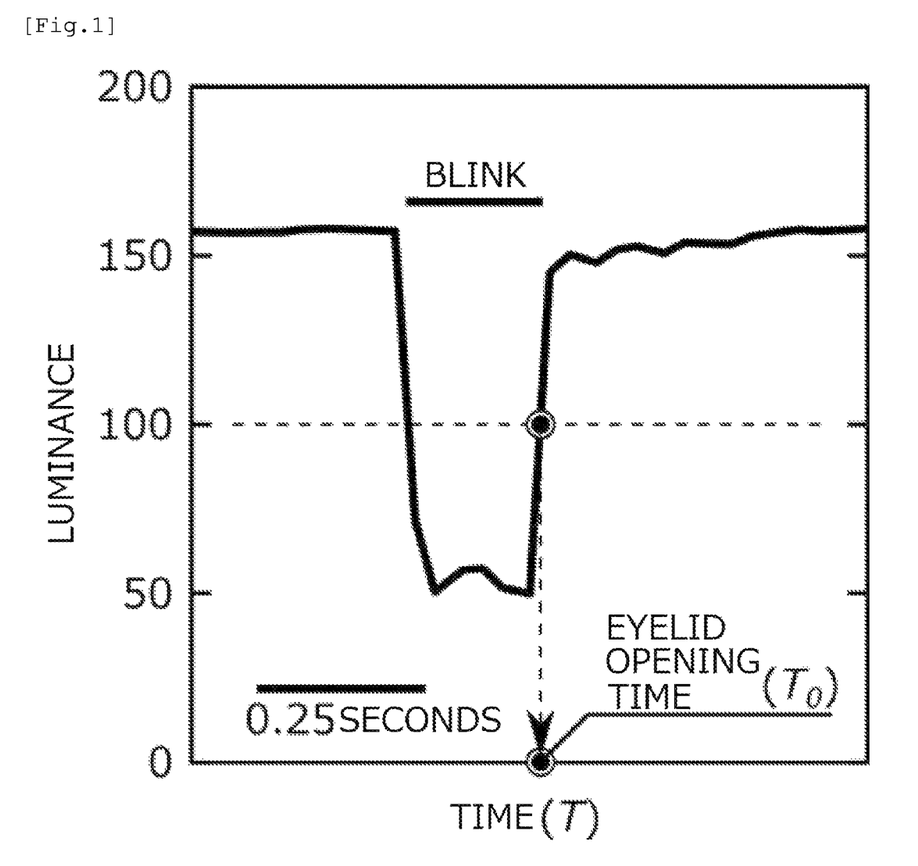
FIG. 1 is a graph showing a change in a luminance value for detecting blink.

Detection of the eyelid opening time using the tear fluid layer interference fringe images will be described. FIG. 1 is a graph in which an average value of the luminance of each of R, G, B (red, blue, green) color elements in a rectangular region of 200×200 pixels in the center of the image was obtained using the tear fluid interference fringe images, and the average value of the luminance is shown in relationship with time. When an eye blinks, there are usually a significant reduction in the luminance by closing the eye and a significant increase in the luminance by opening the eye in the images, which is shown by data in FIG. 1.

In this manner, by using the significant reduction in the luminance average value by closing the eye or the increase in the luminance average value by opening the eye during blinking, a predetermined threshold value of the luminance average value is set and a time when the luminance average value changes by the threshold value or more is detected as the eyelid opening time.

In this processing, the eyelid opening time is detected by the average value of the luminance of each of the RGB color elements. However, the detection method is not limited thereto. Detection may be performed on the basis of any of the luminance of the RGB color elements or a value obtained by performing an appropriate arithmetic operation using the luminance of two or more of the color elements. The luminance of the color image may be directly used, or, for example, the luminance of the image may be converted into a gray scale and used.

The reason why the average value of the luminance in the predetermined region is preferably used for detecting the eyelid opening time is to properly set the threshold value of the luminance. The threshold value may be freely set. However, in such a case, it is difficult to uniformly determine the setting of the threshold value as the acquired tear fluid interference fringe images do not have a constant level of the brightness due to various factors such as an eye state of the subject, for example, a state of the cornea and an amount and length of eyelashes, and a surrounding light quantity. Thus, the threshold value may need to be changed according to the brightness of the tear fluid interference fringe images.

For this reason, the average value of the luminance in the predetermined region in the image is used to set the threshold value, so that it becomes possible to set the proper threshold value appropriate for the image regardless of the brightness (luminance level) of the image itself. Specifically, a median of the minimum value and the maximum value of the luminance average value thus obtained may be set as the threshold value or a value obtained by adding a predetermined value to the minimum value or subtracting a predetermined value from the maximum value may be used as the threshold value. Any method capable of setting a value within a variation range of the luminance average value caused by blinking may be used.

<Extraction of Image at Time when Predetermined Time has Passed>

After detecting the eyelid opening time by the above-described method, the image corresponding to a time when a predetermined time (for example, 5 seconds) has passed from the eyelid opening time is extracted from the tear fluid layer interference fringe images. The extracted image may be a single image (single frame), or a plurality of preceding or succeeding frames with a predetermined number may be acquired.

Note that, although the predetermined time is set to 5 seconds, in a case where a subject is unable to keep the eye open for 5 seconds and closes the eye, it is desirable to have a configuration in which the predetermined time can be changed by a simple operation, allowing an examiner to freely shorten the predetermined time, for example, providing a rotary switch or the like for setting the predetermined time in a tear fluid interference fringe image acquisition device side or providing a unit capable of setting the predetermined time by a simple operation from a computer side. Further, in this case, it is desirable to put information on the predetermined time in supplementary information of the extracted image described below, for example, by displaying the predetermined time small at the corner of the image.

The breakdown of the tear fluid layer is determined using the extracted image at the time when the predetermine time has passed from the eyelid opening time, extracted from the tear fluid layer interference fringe images in this manner. A specific method for determining the tear fluid layer breakdown is performed by determining the breakdown of the tear fluid layer on the basis of the determination value calculated from the color information in the extracted image. A detailed description thereof will be provided below.

<Processing of Extracted Image>

The extracted image is subjected to a determination value calculation processing for determining the tear fluid layer breakdown described below. Specific examples of such a processing include a processing for calculating to which extent the color information varies in the extracted image.

Specifically, the method involves examining the luminance in the RGB color space in each pixel in the predetermined region in the image and evaluating to which extent an intensity of at least one or more of the color elements of red, green, and blue varies in the region.

As the variation, a variance value and a deviation (standard deviation, etc.) obtained from a value of the luminance of each color element or a value (coefficient of variation) obtained by dividing the value such as the variance value and the standard deviation by an average value of the luminance in the pixels in the region may be used. These values may be freely selected and used as needed.

The value indicating the color variation may be calculated in the entire extracted image. However, it is preferable to obtain a diversity of the color information in a local region in which a pixel of interest and pixels adjacent thereto are grouped together. The value indicating the color variation thus obtained has a higher resolution despite having lower immediacy of analysis than when performing the calculation in the entire image. Further, spatial position information is matched with that of the original image, thus contributing to identifying a position and an area of the tear fluid layer breakdown. A detailed description thereof will be provided with reference to FIGS. 3A and B.

FIG. 3A is a schematic diagram in which a standard deviation of the luminance is calculated in a region composed of a total of 9 pixels of 3×3 including a pixel of interest and 8 pixels surrounding the pixel of interest in a target region in an image. Each numerical value in FIG. 3A indicates a numerical value of the luminance in each pixel in a part of the image.

A "region 1" shown in FIG. 3A is composed of a total of 9 pixels (3×3 pixels) including a pixel 1 of interest and pixels surrounding the pixel 1 of interest, and a standard deviation in the region 1 is calculated and outputted in the pixel 1 of interest. FIG. 3B shows a result in which the target region in the image having the luminance shown in FIG. 3A is scanned in this manner.

That is, the target region (entire or a desired part of the image) in the extracted image obtained as described above is scanned using a filter for outputting a standard deviation of the color information such as the luminance in the local region composed of a pixel of interest and predetermined pixels having the pixel of interest as a center to the pixel of interest, and the standard deviation outputted in each pixel is stored.

Figure 3:
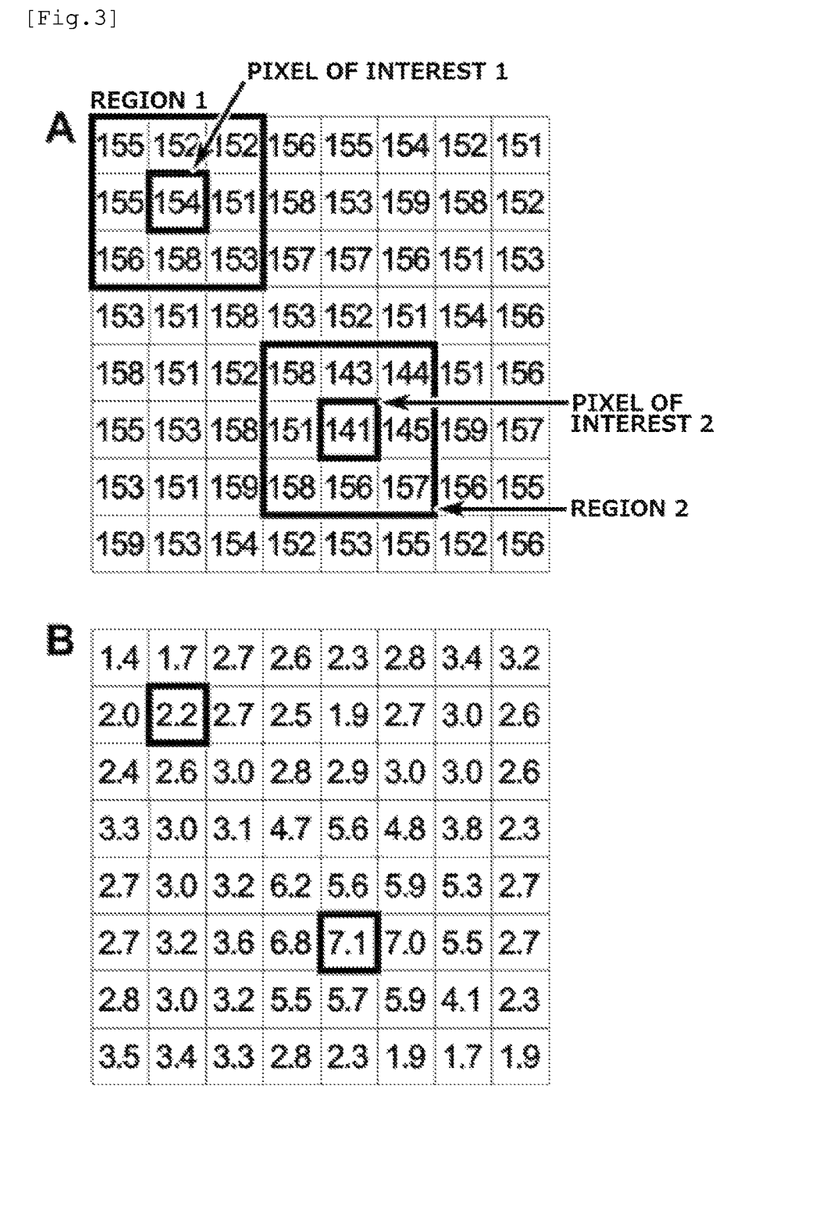
FIG. 3 is diagram illustrating an example of color information (luminance value) in each pixel in a part of a target region in an extracted image extracted from the tear fluid layer interference fringe images, and a local region for calculating a determination value and a calculated result of the determination value.

Examining specific numerical values in FIGS. 3A and B, the standard deviation outputted in the pixel 1 of interest in the region 1 is as small as "2.2," while the value outputted in the pixel 2 of interest in the region 2 is as large as "7.1." In principle, the color variation tends to be higher as the state of the tear fluid layer becomes worse. In data shown in FIG. 3, the color variation is higher in the region 2 than in the region 1, thus, it can be determined that the state of the tear fluid layer is worse in the region 2.

Note that, if a subject has a severe symptom of the widespread tear fluid layer breakdown, for example, as indicated by dry eye severity grade 5, the tear fluid layer breakdown cannot be always properly determined only by the numerical value calculated as the variance or the standard deviation of the color information such as the luminance as described above. A tear fluid layer breakdown site has the constant luminance with small variation as compare with a site where there is no breakdown. Thus, if the tear fluid layer breakdown site is widespread, there is an increase in the number of sites where the value indicating the variation represented by the variance or the standard deviation described above does not increase, possibly resulting in failure to detect the tear fluid breakdown or erroneous determination as a mild symptom which is different from reality.

Thus, as shown by the following formula, a numerical value obtained by dividing the value represented by the variance or the standard deviation of the luminance obtained as described above by the average value of the luminance in that region may be used as the coefficient of variation.

Coefficient of variation=standard deviation of luminance/luminance average value [Formula 1]

Note that, in the foregoing description, in FIG. 3, the value indicating the color variation such as the standard deviation or the coefficient of variation in the local region composed of a pixel of interest and pixels surrounding the pixel of interest is outputted in each pixel of interest. However, instead of performing outputting in each pixel of interest, the local region may be regarded as a section and the standard deviation may be outputted in each section. Further, needless to say, such a region or section is not limited to the total of 9 pixels of 3×3 and may be a group having any number of the pixels.

As described above, the value indicating the color variation is obtained by calculating the variation, that is, the variance or the deviation such as the standard deviation, of the color information (luminance, etc.) in the predetermined region. Further, other than these values, a value obtained by dividing the value indicating the variation of the color information in the predetermined region by the average value of the color information in the predetermined region, that is, the coefficient of variation, is used as the value indicating the color variation.

<Determination of Tear Fluid Layer Breakdown>

The breakdown of the tear fluid layer is determined on the basis of the value indicating the color variation such as the variance, the standard deviation, and the coefficient of variation obtained from the extracted image as described above. For example, the occurrence of the breakdown of the tear fluid layer is determined, by counting the number of the pixels or sections in which the value indicating the color variation such as the standard deviation is equal to or higher than a predetermined threshold value, if the counted number is equal to or higher than a predetermined threshold value.

As another method, for example, the occurrence of the breakdown of the tear fluid layer may be determined, by calculating an area of the pixels or sections in which the value indicating the color variation such as the standard deviation is equal to or higher than a predetermined threshold value, if the area is equal to or higher than a predetermined threshold value.

Further, determination may be based on a ratio of the pixels or sections in which the value indicating the color variation such as the standard deviation is equal to or higher than a predetermined threshold value with respect to the entire scanning target region in the extracted image. The breakdown of the tear fluid layer may be determined if a ratio of the number or area of the pixels in which the value indicating the color variation is equal to or higher than a predetermined threshold value with respect to the number or area of the pixels in the entire scanning target region in the extracted image is equal to or higher than a predetermined level.

However, it is difficult to preclude the possibility that the calculated value indicating the color variation includes a noise due to, for example, the improper original color information in the extracted image. Thus, even if the pixel or section is determined to have the value indicating the color variation equal to or higher than a predetermined threshold value, unless satisfying a predetermined size (area) as one continuous region, such a pixel or section may be excluded.

In the foregoing description, first, the eyelid opening time (t0) of the subject is detected using the tear fluid layer interference fringe images, the image corresponding to the time when a predetermined time has passed from the eyelid opening time (t0) is extracted, and the tear fluid layer breakdown is determined using the extracted image. As described above, in recent years, the diagnosis standard in which dry eye is diagnosed simply by having "BUT" of 5 seconds or less is adopted in Asia regions including Japan. That is, in accordance with this new standard, it is meant that dry eye can be diagnosed by determining the tear fluid breakdown using the extracted image 5 seconds after the eyelid opening time (t0), and thus a simpler and more efficient diagnosis of dry eye is made possible without necessity of precisely measuring "BUT" as before.

Example 2

In Example 1, the tear fluid breakdown was determined on the basis of the value indicating the color variation as the determination value calculated from the color information. However, the tear fluid breakdown may be determined as follows instead of using the value indicating the color variation as the determination value.

The tear fluid layer breakdown site is characterized by having a high whiteness degree in general and a higher value of the luminance than a site where there is no breakdown. Thus, a luminance average in the pixels in the local region in the extracted image is calculated and the pixels in the local region having the luminance equal to or higher than the luminance average value are extracted.

The number of the extracted pixels is counted, and the tear fluid layer breakdown is determined if the counted number is equal to or higher than a predetermined threshold value. Further, the tear fluid layer breakdown may be determined if an area of the extracted pixels is equal to or more than a certain level or a ratio thereof with respect to the target region is equal to or higher than a certain level, instead of using the number of the pixels.

Using the characteristics in which the tear fluid layer breakdown site has a high whiteness degree in general and a higher value of the luminance than a site where there is no breakdown, a method of extracting an outline of the breakdown site may be used. Extracting the outline allows the breakdown site to be labeled. The labeling is a method in which the extracted region is numbered, so that information on a size, a shape, or the like of each region can be obtained. Using a size or a shape of the extracted region as an index makes it possible to exclude a part which should not be extracted as a breakdown site. Whether the image includes a breakdown site can be determined by the number, an area, or a shape of the extracted breakdown region.

As a method for extracting an outline of the breakdown site, a method using an image processing filter such as a differential filter, Sobel filter, and Laplace filter, Canny edge extraction method, and the like can be used.

While the present invention has been described above, it is to be understood that the present invention is not limited to the above-described examples and can be modified and embodied in various aspects.

For example, in calculating the value indicating the color variation, the original image may be appropriately magnified or reduced. As a magnification method, a method in which a gap of the luminance of the pixel is interpolated by a function, such as a bilinear method, a bicubic method, and the Lanczos method, is preferable. As an effect of magnification, a state of each site can be acquired in more detail. On the other hand, as a reduction method, any method including a nearest-neighbor method, a bilinear method, a bicubic method, and the Lanczos method may be used. As an effect of reduction, shortening of analysis time is mentioned. These methods may be selected and used according to the need.

INDUSTRIAL APPLICABILITY

The present invention can be used as a method for objectively digitalizing the state of the tear fluid layer undergoing breakdown in the diagnosis of dry eye using the tear fluid layer interference fringe image without relying on the ability of the observer. In particular, in accordance with the recently adopted new standard in which dry eye is determined by the presence or the absence of the tear fluid layer breakdown 5 seconds after the eyelid opening time, a simple and efficient determination can be achieved in a non-invasive manner.

The invention claimed is:

1. A tear fluid layer evaluation method comprising:
   a step of detecting a time when color information in a predetermined region in a tear fluid layer interference fringe image changes by a threshold value or more as an eyelid opening time;
   a step of extracting an image at the time when the predetermined time has passed from the eyelid opening time as an extracted image from the tear fluid interference fringe images;
   a determination value calculation step of calculating a determination value from the color information in a pixel in a local region by scanning a predetermined target region in the extracted image;
   a step of detecting a corresponding pixel by comparing the calculated determination value and a threshold value; and
   an evaluation step of evaluating tear fluid layer breakdown by comparing the detected pixel and a threshold value.

2. The tear fluid layer evaluation method according to claim 1, wherein the determination value is a value indicating color variation calculated from the color information in the local region.

3. The tear fluid layer evaluation method according to claim 2, wherein the value indicating the color variation is a value calculated as a variance or a deviation in the local region.

4. The tear fluid layer evaluation method according to claim 2, wherein the determination value is a value obtained by dividing the value indicating the color variation in the local region by an average value of the color information in the local region.

5. The tear fluid layer evaluation method according to claim 1, wherein the determination value is an average value of the color information in the local region.

6. The tear fluid layer evaluation method according to claim 1, wherein the predetermined time is 5 seconds.

7. The tear fluid layer evaluation method according to claim 1, comprising a predetermined time change step of allowing an examiner to change the predetermined time from the eyelid opening time.

8. The tear fluid layer evaluation method according to claim 1, wherein the extracted image is extracted by acquiring the image at the time when the predetermine time has passed and its preceding or succeeding images having a plurality of frames with a predetermined number.

9. A computer program for causing a computer to execute the respective steps according to claim 1.

10. A tear fluid layer evaluation device executing the method according to claim 1.

* * * * *